(12) United States Patent
Henspeter

(10) Patent No.: US 9,666,321 B2
(45) Date of Patent: May 30, 2017

(54) OPTICAL CAPTURE AND ISOLATION OF CIRCULATING TUMOR CELLS IN A MICRO-FLUIDIC DEVICE UTILIZING SIZE SELECTIVE TRAPPING WITH OPTICAL COGWHEEL TWEEZERS

(71) Applicant: International Business Machines Corporation, Armonk, NY (US)

(72) Inventor: Justin E. Henspeter, Kasson, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/746,547

(22) Filed: Jun. 22, 2015

(65) Prior Publication Data

US 2016/0299045 A1 Oct. 13, 2016

Related U.S. Application Data

(63) Continuation of application No. 14/682,710, filed on Apr. 9, 2015.

(51) Int. Cl.
*G01N 21/64* (2006.01)
*G01N 1/40* (2006.01)
(Continued)

(52) U.S. Cl.
CPC .............. *G21K 1/006* (2013.01); *G01N 1/40* (2013.01); *G01N 15/00* (2013.01);
(Continued)

(58) Field of Classification Search
CPC .......... G01N 1/4077; G01N 1/40; G01N 1/48; G01N 33/4833; G01N 33/483;
(Continued)

(56) References Cited

U.S. PATENT DOCUMENTS 7,781,260 B2 8/2010 Sane et al.
2004/0072278 A1* 4/2004 Chou ................ B01L 3/502761
435/29
(Continued)

FOREIGN PATENT DOCUMENTS

BG 200802017 A1 4/2009
JP 5589364 B2 9/2014
WO 2014195271 A1 12/2014

OTHER PUBLICATIONS

Patent application entitled "Optical Capture and Isolation of Circulating Tumor Cells in a Micro-Fluidic Device Utilizing Size Selective Trapping With Optical Cogwheel Tweezers", U.S. Appl. No. 14/682,710, filed Apr. 9, 2015.

*Primary Examiner* — Christine T Mui
(74) *Attorney, Agent, or Firm* — Patterson + Sheridan, LLP

(57) ABSTRACT

Embodiments generally relate to devices, systems and methods for separating CTCs from blood cells using optical trapping, such as use of optical cogwheel tweezers. Through a pre-filtration process, using optical cogwheel tweezers, desired cells from a cell sample can be filtered from a relatively dilute sample. The filtered sample can then be analyzed by more precise means to determine overall concentrations from the original sample while maintaining cell viability.

9 Claims, 5 Drawing Sheets

(51) Int. Cl.
  *G21K 1/00*    (2006.01)
  *G01N 33/483*  (2006.01)
  *G01N 15/00*   (2006.01)
  *G01N 15/10*   (2006.01)
  *G01N 15/14*   (2006.01)

(52) U.S. Cl.
  CPC ..... *G01N 33/4833* (2013.01); *G01N 15/1459* (2013.01); *G01N 2015/1006* (2013.01); *G01N 2015/149* (2013.01)

(58) Field of Classification Search
  CPC .... G01N 33/48; G01N 21/6486; G01N 21/64; G01N 21/63; Y10T 436/25; Y10T 436/25375
  USPC .................................................. 436/177, 174
  See application file for complete search history.

(56)  References Cited

U.S. PATENT DOCUMENTS

2009/0065932 A1    3/2009  Sane et al.
  2009/0076198 A1    3/2009  Giesenberg et al.
  2010/0249306 A1    9/2010  Berndt et al.
  2010/0282984 A1*  11/2010  Kreysing ................ B03C 5/026
                                                          250/492.1
  2014/0061902 A1    3/2014  Ramalingam et al.
  2014/0370313 A1   12/2014  Thomas et al.

* cited by examiner

OPTICAL CAPTURE AND ISOLATION OF CIRCULATING TUMOR CELLS IN A MICRO-FLUIDIC DEVICE UTILIZING SIZE SELECTIVE TRAPPING WITH OPTICAL COGWHEEL TWEEZERS

CROSS-REFERENCE TO RELATED APPLICATIONS

This application is a continuation of co-pending U.S. patent application Ser. No. 14/682,710, filed Apr. 9, 2015. The aforementioned related patent application is herein incorporated by reference in its entirety.

BACKGROUND

Embodiments described herein generally relate to detection of circulating tumor cells.

Cancer remains a major public health issue in the United States as well as in other regions of the world. One in every four deaths in the United States can be attributed to one or more types of cancer. According to statistical data available from the National Center for Health Statistics and the National Cancer Institute's Surveillance, Epidemiology, and End Results (SEER) Program for the years from 1930 to 2010, men have roughly a 44% chance of developing cancer in their lifetimes, as compared with a 38% chance for women. Early detection is the key to effective diagnosis, treatment and increased survival rate.

It is well known that the major cause of cancer-associated mortality (upwards of 90%) is tumor metastasis. Tumor metastasis is the spread of tumor cells from a primary tumor in a tissue of origin to a secondary tissue in the organism, by route of tumor cells which are dislodged or otherwise released from the tumor (e.g., circulating tumor cells or CTCs). CTCs are cells that have been released from the primary tumor and enter the vasculature or lymphatic system and circulate in the bloodstream. CTCs can affix themselves, through a variety of means, to the secondary tissue and grow in distant (anatomically speaking) locations, such as vital organs. CTCs have been detected in several epithelial cancers including breast, prostate, ovarian, lung and colon cancer. For women, the combination of breast, ovarian, lung and colon cancer equates to roughly 50% of the estimated new cancer cases that will result in death in the United States alone. For men, considering the combination of breast, prostate, lung and colon cancer, this number is just slightly lower at 46%. As such, detecting CTCs in the early stages of metastatic diseases would be very helpful relative to defining a well-timed and more effective therapy. As CTCs are directly related to cancer progression and are not detected in healthy patients or patients with non-malignant cancers, lower numbers of CTCs in the bloodstream equate to longer survival time and decreased severity of prognosis. The biggest challenge surrounding the detection of CTCs is the extremely low concentration in which these cells exist in the early stages of metastasis. In these early stages, CTCs can exist in extremely low concentrations (<10 CTCs/mL of blood). Further, it becomes very difficult to accurately detect CTCs in the presence of approximately 10 million leukocytes and approximately 5 billion hemocytes in 1 mL of whole blood.

To date, many assays have been developed to assist in the detection of CTCs in a patient's peripheral blood, which is blood obtained from circulation which is remote from the heart. One assay for the detection of CTCs called CELLSEARCH CTC, available from Janssen Diagnostics in Raritan, N.J. This system utilizes density gradient centrifugation to separate CTCs, based on the fact that CTCs are larger in size than leukocytes and hemocytes. The separation is followed by further purification processes including immunomagnetic cell enrichment using antibodies targeting an epithelial cell adhesion molecule (EpCAM), nucleus labeling with fluorescent dye and flow cytometry. One concern with such an assay lies in that of the filtration as filter edges can damage trapped cells, leading to lower cell viability. Another concern is possible loss of CTCs in the centrifugation step. Finally, the further purification relies on surface expression of EpCAM, which may be downregulated in some CTCs. All of the above deficiencies can lead to false negatives, especially in early detection. Additionally, methods such as that of CELLSEARCH CTC require large volumes of blood (7.5 mL), in an attempt to overcome the above noted deficiencies.

Conventional flow cytometry is a laser-based, biophysical technology employed in cell counting, cell sorting, biomarker detection and protein engineering, by suspending cells in a stream of fluid and passing them by optical detection of fluorescence. The optical detection of flow cytometry is accomplished through alignment of cells into a single file line where a tightly focused laser is used to detect scattering and fluorescent light from individual cells. A Photo Multiplier Tube (PMT) is used to convert and amplify the photons emitted for detection by one or more fluorescence detectors. Although this method is very good in terms of accuracy and multi-parameter qualification, throughput is its largest shortfall. Limited throughput is especially important when taking into consideration a system for point-of-care usage, such as for use in a clinical setting. CTC viability is another of this method's drawbacks as well as capture efficiency. Further, low flow rates (in the vicinity of 1-2 mL/h) are standard requiring many hours for the completion of analysis.

Another implementation which helps to address the throughput issue faced by the Cell Search method is that of Fiber-optic Array Scanning Technology, or FAST. This assay claims detection of rare CTCs at a rate of nearly 500 times faster than that of ADM (Automated Digital Microscopy) with comparable sensitivity and improved specificity. In this method, a laser is used for improved exposure time, but the key innovation claimed by the FAST method is the use of an array of optical fibers that forms a wide collection aperture and 100 times field of view improvement over standard ADM.

Although a reduction in image resolution is suffered by the FAST assay, it remains adequate for the detection of fluorescently labeled cells. The large field of view is achieved by an array of optical fibers with asymmetric ends. The collected emission from the fiber array is subsequently collimated and then filtered using dichroic filters. The signal is then detected by a PMT. The focused beam from the laser is transformed into an elliptical spot via the galvanometer and F-Theta lens (in the absence of distortion, the position of the focused spot is dependent on the product of the Focal Length and the tangent of the deflection angle). Although this assay provides a significant increase in throughput over that of independent flow cytometry or the previously described Cell Search method, manual intervention requiring additional study of suspect cells using ADM remains necessary to differentiate false positives and/or negatives. Although the FAST assay provides a much faster method of CTC detection, the clinical setting can still benefit from further speed improvements and increases to both sensitivity and specificity in detection.

As such, there is a need in the art for devices, systems and methods to improve throughput and detection sensitivity and specificity in CTC detection.

SUMMARY

Embodiments described herein generally relate to devices, methods and systems for detection of a desired cell type in a biological sample. In one embodiment, a cell sorting device can include a sample basin, the sample basin having a first trap position in optical connection with a first coherent radiation source, the first coherent radiation source for producing one or more optical cogwheel tweezers; a sample channel having a first end and a second end, the first end in communication with the sample basin; an exhaust channel having a first exhaust end and a second exhaust end, the first exhaust end in communication with the sample basin; a flow control device in communication with the sample basin, the flow control device controlling flow between the sample basin and the sample channel or the exhaust channel; a second coherent radiation source positioned to deliver radiation at a second trap position of the sample channel, the second trap position beginning after the first end; a radiation detection device in optical communication with the second trap position; a holding tank in connection with the second end, and an exhaust tank in connection with the exhaust channel.

In another embodiment, a method of cell sorting can include forming one or more optical cogwheel tweezers at a first position, the optical cogwheel tweezers having an aperture; size-selectively filtering a biological sample, the filtering comprising delivering a biological sample through the optical cogwheel tweezers at the first position, the biological sample comprising a cell sample, the optical cogwheel tweezers trapping a first portion of the cell sample from the biological sample and creating a first effluent; directing the first effluent to an exhaust channel and the first portion of the cell sample to a sample channel, the exhaust channel connecting to an exhaust tank; directing coherent radiant energy at a point along the sample channel, the first portion of the cell sample providing fluorescence data in response to the coherent radiant energy; separating the first portion of the cell sample into a second cell sample and a second effluent using the fluorescence data; delivering the secondary cell sample to a holding tank; and delivering the second effluent to the exhaust tank; and repeating the size-selective filtering one or more times using the first effluent and the second effluent collected in exhaust tank.

In another embodiment, a cell sorting system can include a sample reservoir in connection with the sample basin, the sample reservoir configured to deliver a biological sample to the sample basin; a sample basin having a first trap position, the sample basin configured to receive a sample; a coherent radiation source in optical connection with the sample basin, the sample basin having a first trap position in optical connection with a coherent radiation source, the coherent radiation source configured to form an optical cogwheel tweezers at the first trap position; a sample channel having a first end and a second end, the first end in communication with the sample basin, the sample channel configured to transport a cell sample of the biological sample therethrough; and deliver the cell sample to a holding tank; an exhaust channel having a first exhaust end and a second exhaust end, the first exhaust end in communication with the sample basin, the exhaust channel configured to transport an effluent of the biological sample therethrough; and deliver the effluent to an exhaust tank; a flow control device in communication with the sample basin, the flow control device configured to direct the cell sample to the sample channel; and direct the effluent to the exhaust channel; a second coherent radiation source positioned to deliver radiation at a second trap position of the sample channel, the second trap position beginning after the first end, the second coherent radiation configured to trap the cell sample; and create fluorescence from the cell sample; and a radiation detection device in optical communication with the second trap position.

BRIEF DESCRIPTION OF THE SEVERAL VIEWS OF THE DRAWINGS

So that the manner in which the above recited features of the present devices, systems and methods can be understood in detail, a more particular description of the devices, systems and methods, briefly summarized above, may be had by reference to embodiments, some of which are illustrated in the appended drawings. It is to be noted, however, that the appended drawings illustrate only typical embodiments and are therefore not to be considered limiting of its scope, for the devices, systems and methods may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments described herein generally relate to separating CTCs from blood cells using optical trapping, such as using optical cogwheel tweezers. Optical cogwheel tweezers are collinear superpositions of two Laguerre-Gaussian beams (doughnut beams) of equal and opposite helical index, and can be generated using diffractive optical elements, such as a high resolution refractive spatial light modulator (SLM). Laguerre-Gaussian beams exhibit characteristic light intensity modulation around the circumference of a sphere. Optical cogwheel tweezers are able to trap only those particles of size exceeding the 'ring' diameter by certain amount, thus enabling a passive sorting for particles of differing sizes. Optical cogwheel tweezers can be used to manipulate and move microscopic particles, including biological and molecular structures. In this application, optical cogwheel tweezers are employed to separate cells based on differing size, since CTCs are significantly larger than either hemocytes or leukocytes.

Figure 1A:
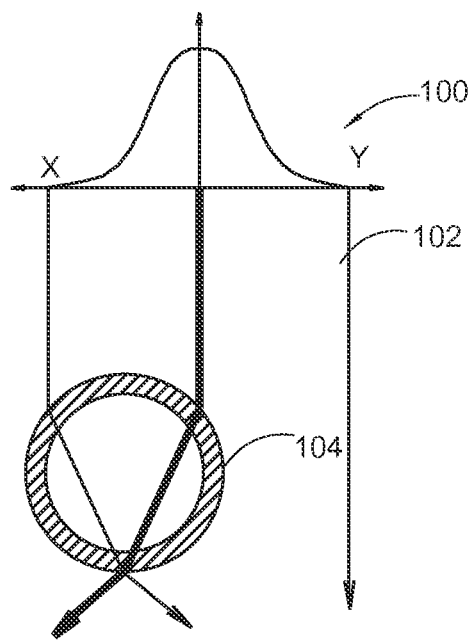
FIGS. 1A and 1B illustrate the concept of optical trapping.
Figure 1B:
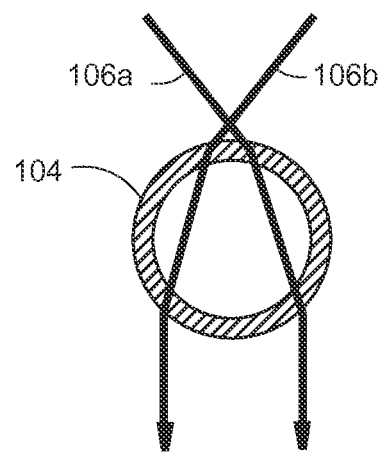

The concept of optical trapping is illustrated in FIGS. 1A and 1B. In FIG. 1A, radiant energy 100 with a Gaussian intensity distribution 102 is focused on a spherical bead 104. The bead 104 may be representative of a CTC in a biological sample, such as a blood sample. In this example, the radiant energy 100 is refracted, and thus deflected to the left, which results in development of a force that pushes the bead to the right due to the net dipole force. The bead will eventually come to rest directly in line with the intensity maximum at the center of the beam, where net deflection forces laterally (i.e., x and y) are balanced. Thus, the bead becomes "trapped" at the maximum of the Gaussian beam.

In FIG. 1B, the bead 104 is vertically trapped due to the radiant energy as follows: Consider two Gaussian beams 106a and 106b configured to converge initially at a point in front of the bead. The bead 104 will be drawn to the maximum intensity point (as explained for x-y trapping) at the intersection of both beams 106a and 106b, which is generally upward, but also has lateral components pertaining to each beam, since each beam is directed at an angle toward the particle. The two horizontal components of force may cancel, leaving a net upward vertical force. The bead experiences a net vertical force upward until the point of convergence of the two beams reaches a point substantially near the center of the bead, at which point the net vertical forces of the incident and exiting beams may cancel. In this circumstance, the bead is "trapped" in the z-direction as well as the x-y direction. A single beam that converges to a focal point will similarly trap the bead at the focal point, i.e., the point of highest optical power density.

While conventional optical trapping generally uses highly focused Gaussian beams, adapting the shapes of such light beams may be more useful for control of particles, such as during a size selection process. Beams shaped to have one or more intensity minima and one or more high intensity maximum may be configured to select particles from a flowing sample based on size while rejecting particles that do not match the size criteria. For example, Laguerre-Gaussian (LG) profile beams have intensity profiles which include on-axis minima and consist of a series of concentric rings. LG beams shaped in this manner may be used to trap particles in the high intensity portion of the ring(s) and remove particles from the central minimum portion. Embodiments disclosed herein are more clearly described with reference to the figures below.

FIG. 2 depicts a cell sorting device 200 according to one embodiment. The cell sorting device 200 includes a substrate 202. In one example, the substrate 202 may have a substantially planar surface having one or more components formed thereon or integrated therein. The substrate 202 can be a material such as crystalline silicon, silicon oxide, strained silicon, silicon germanium, doped or undoped polysilicon, doped or undoped silicon wafers and patterned or non-patterned wafers silicon on insulator (SOI), carbon doped silicon oxides, silicon nitride, doped silicon, germanium, gallium arsenide, glass, sapphire or other similar materials. The substrate 202 may have dimensions such that the components of the cell sorting device 200 may be positioned according to need or desire, shown here as a rectangular panel with a length to width ratio of approximately 3:1.

The cell sorting device 200 includes a sample basin 204. The sample basin 204 is a partially enclosed region which receives a sample for cell sorting. The sample basin 204 receives the biological sample which distributes throughout the basin 204 as bounded by the walls. The sample basin 204 can be attached to the substrate 202. The sample basin 204 can also be formed into the substrate 202. The sample basin 204, shown as rectangular, can be of any shape. In one embodiment, the sample basin is divided into two or more sub basins (not shown). The sample basin 204 has at least one first trap position 205 and at least one coherent radiation source 206 associated with each trap position. The first trap position 205 is the position in the sample basin 204 where the optical cogwheel tweezers are formed.

The coherent radiation source 206 is a source of radiation in which the phase relationship between sections of the wave at different locations is not random. In one example, the coherent radiation source 206 is a laser beam which includes fiber optics such that the beam is split and delivered to multiple sites on the substrate 202. Shown here, the fiber optics deliver the coherent radiation from the coherent radiation source to eight (8) sites on the substrate. The coherent radiation source 206 can include one or more adaptive elements such that the laser can be reshaped, split, converged or redirected. Adaptive elements can include fiber optics, spatial light modulators, mirrors, optical lenses or other optics affecting devices. In another embodiment, multiple coherent radiation sources 206 are used with or without an adaptive element. The coherent radiation source 206 produces two collinear beams which are directed at the first trap position radiation for use in the creation of optical cogwheel tweezers at the first trap position 205.

Optical cogwheel tweezers, as used herein, are collinear superpositions of two Laguerre-Gaussian beams. Laguerre-Gaussian beams are Gaussian profile radiation, produced by the coherent radiation source 206, having a screw phase angular momentum, which creates both the hollow center and the circular symmetry of the resulting beam. Laguerre-Gaussian beams are created by diffraction of coherent radiant energy which has a Gaussian energy profile at a high resolution refractive spatial light modulator (SLM). Laguerre-Gaussian beams can transfer orbital momentum to a trapped particle and can be used to trap particles with a refractive index higher than that of the surrounding medium, such as CTCs. To prevent the orbital rotation, collinear superpositions of two Laguerre-Gaussian beams having an opposite rotation are used to create the optical cogwheel tweezers.

The cell sorting device 200 has at least one sample channel 208 fluidly connected with the sample basin 204, shown here as eight (8) sample channels 208 associated with each trap position. The sample channel 208 is a channel having a width or a diameter which allows for delivery of cells in a biological sample in a single file line and without shearing of the cells. In one embodiment, the sample channel 208 has a width or diameter of less than about 50 µm, such as between about 10 µm and about 30 µm. The sample channel 208 may have an internal and/or an external shape which is cuboid, cylindrical or other shape. In one embodiment, the sample channel 208 is a cylinder which extends the length of the substrate 202. The sample channel 208 may be large enough to deliver the single file line of cells surrounded by a sheath fluid. The sample channel 208 may be formed into the substrate 202 or may be positioned on the substrate 202. Further, the sample channel 208 may have the same composition as the substrate or any other fluid-stable composition such that the biological sample can be delivered therethrough.

The cell sorting device 200 can further include an exhaust channel 209. The exhaust channel 209 is a channel for receiving the biological material that is not selected during the trapping process. The exhaust channel 209 can have dimensions, compositions and shapes as described with reference to the sample channel 208. The exhaust channel 209 extends from and is fluidly connected to the sample basin 204. The exhaust channel 209, though shown as being slightly smaller than the sample channel 208, may have the same dimensions, shapes and compositions as the sample channel 208. The exhaust channel 209 can be formed on or in the substrate 202. Each sample channel 208 can have a separate exhaust channel 209, as shown here. However, more or fewer exhaust channels 209 may be used as compared to the number of sample channels 208.

The cell sorting device 200 further includes a flow control device 207. The flow control device 207 can include devices to separate the flow of the biological sample based on trapping at the first trap position 205. The flow control device 207 is positioned to deflect a cell or a portion of the biological sample to either the sample channel 208 or the exhaust channel 209. The flow control device 207 can include physical barriers, such as a microactuator with a deflection plate, or electrical deflection, such as a dielectrophoresis device.

Dielectrophoresis (DEP) occurs when a polarizable particle is suspended in a non-uniform electric field. The electric field polarizes the particle, and the poles then experience a force along the field lines, which can be either attractive or repulsive according to the orientation on the dipole. Since the field is non-uniform, the pole experiencing the greatest electric field will dominate over the other, and the particle will move. The electrical fields can be created using electrodes. Thus, by presenting the non-uniform charge to the polarizable particles of the biological sample, portions of the biological sample can be deflected to either the sample channel 208 or the exhaust channel 209.

Shown here, the flow control device 207 is a dielectrophoresis device. The flow control device 207, positioned in front of each of the sample channel 208 and exhaust channel 209 entrances, has a positive electrode 222a and negative electrodes 222b and 222c. The positive electrode 222a provides a positive charge to all particles in the biological sample. Negative electrode 222b is on by default, such that all particles are directed to the exhaust channel. When an object, such as a CTC, is captured from the biological sample in the optical cogwheel trap at the first trap position 205, the capture is detected, such as by a radiation detection device. The radiation detection device can be a photodetector. The detection causes the negative electrode 222c to be turned on. When the negative electrode 222c is on, the negative electrode 222b can be turned off or be left on, with the negative electrode 222b having a stronger negative charge than the negative electrode 222c. As such, the negative electrode 222b will attract the positively charged particle, and move down the sample channel 208 based on capillary forces, when the particle is trapped at the first trap position. But otherwise, the particles will be attracted to the negative electrode 222c and be moved down the exhaust channel 209 by capillary forces.

The cell sorting device 200 can further include a second trap position 214. The second trap position 214 is depicted here as formed along the sample channel 208. The second trap position 214 receives radiation from a second coherent radiation source 210. The second coherent radiation source 210 can be a radiation source, or components thereof, as described with reference to the first coherent radiation source 206. The second trap position 214 can receive radiation that forms a second optical cogwheel trap. Here, the second cogwheel trap can be more finely attuned to possible sizes for the sample, such as having a diameter of between about 12 μm and about 25 μm. Finer attuned cogwheel size will allow for either internal selection between sizes of cells, such as when there is a possibility of multiple CTCs in a sample. To change the size of the cogwheel, the angular momentum, the phase, or the amplitude of the Laguerre Gaussian beams can be modulated. In further embodiments, combinations of the angular momentum, the phase, or the amplitude are modulated. In another embodiment, the second trap position 214 receives radiation that forms a two dimensional trap, using a standard Gaussian distribution radiation source.

A radiation detection device 212 is positioned in optical connection with the second trap positions 214 and the second coherent radiation source 210. The radiation detection device 212 may be a photodetector, such as the type of photodetector used in fluorescence activated cell sorting. The radiation detection device 212 may be integrated with or positioned over the substrate 202. The radiation detection device may be positioned to receive radiation reflected from or produced at the second trap position 214.

The cell sorting device 200 may further include a holding tank 216 and an exhaust tank 220. The holding tank 216 can be fluidly connected with the sample channel 208. The exhaust tank 220 can be fluidly connected with the exhaust channel 209. An interconnecting channel 218 may be formed between the sample channel 208 and the exhaust channel 209. The interconnecting channel 218 allows excluded portions from the biological sample, as passing through the sample channel 208, to exit the sample channel 208 and enter the exhaust channel 209 after a second separation at the second trap position 214. The second separation offers a further opportunity to refine the sample, such that the sample primarily includes CTCs and not extraneous components of the biological sample.

In operation, a biological sample, which has been treated with a fluorophore, is delivered from a sample reservoir to the sample basin 204. The sample basin 204 has one or more optical cogwheel tweezers formed using the first coherent radiation source 206 at the first trap position 205. The biological sample passes through the optical cogwheel tweezers, the optical cogwheel tweezers selecting cells or other components which are larger than the selected size. In the case of CTCs, the selected size would be a diameter between about 10 μm and about 30 μm. The selected or trapped CTCs are directed down the sample channel 208 using the flow control device 207 while the remaining portions of the biological sample, including hemocytes and leukocytes, are directed down the exhaust channel 209.

The CTCs are delivered single file through the sample channel 208 to the second trap positions 214. The second coherent radiation source 210 delivers radiation to the second trap position 214. In embodiments using the second optical cogwheel tweezers, the fluorophore and the radiation detection device 212 are unnecessary. The size selected CTCs will be allowed to continue through the sample channel 208. The remaining components in the sample channel 208 are then redirected down the interconnecting channel 218 using a second flow control device (not shown). The interconnecting channel 218 delivers the remaining components to the exhaust channel 209, which collects into the exhaust tank 220. The CTCs are delivered through the sample channel 208 and into the holding tank 216.

The contents of the exhaust tank 220 can be processed one or more times by the same system as above to assure that all CTCs are collected. Once processing is complete, the sample from the holding tank 216 can be collected for further processing, such as culturing, mutational or expression analysis or other processing.

Figure 2A:
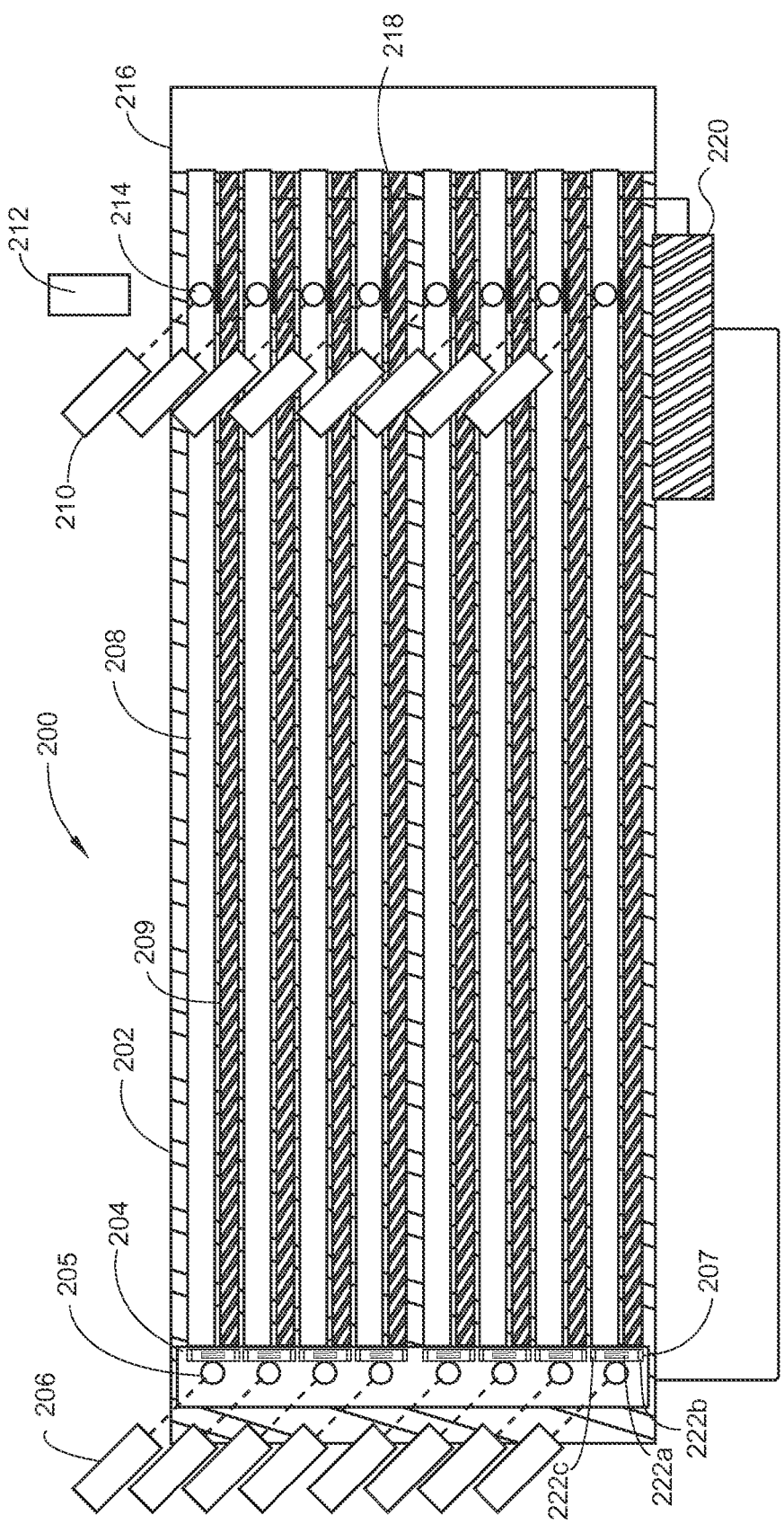
FIG. 2A depicts a cell sorting device according to one embodiment.
Figure 2B:
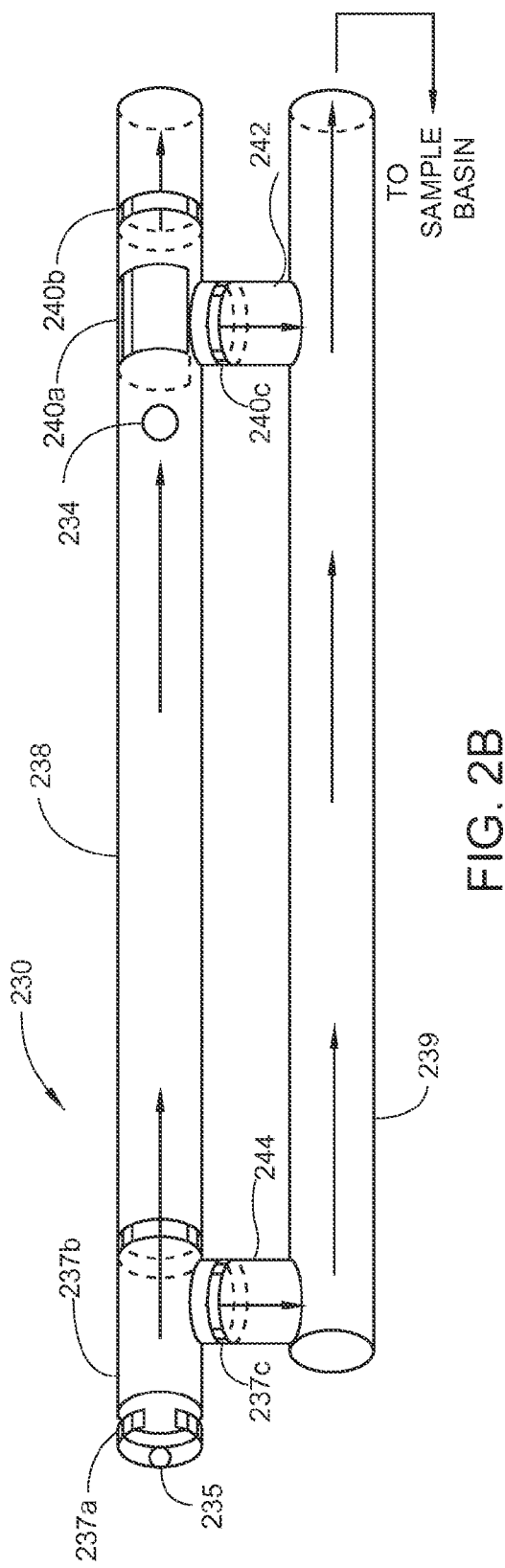
FIGS. 2B-2D depict channel systems according to further embodiments.

FIG. 2B describes a channel system 230 according to one embodiment. The "channel system" is another name for the combination of the trap positions, the channels and the flow control devices described above. Thus, the channel system 230 is an alternate embodiment which can be used in combination with or as a replacement for the channel system described with reference to FIG. 2A. The channel system 230 includes a first trap position 235, a first positive electrode 237a, first negative electrodes 237b and 237c, a sample channel 238, a first intermediate channel 244, a second trap position 234, a second positive electrode 240a, second negative electrodes 240b and 240c, and a second intermediate channel 242.

The biological sample is received in the sample basin 204, described with reference to FIG. 2A. The biological sample flows into the first trap position 235. The first trap position 235 receives optical cogwheel tweezers as described above.

The positive electrode 237a is formed or positioned at the opening of the sample channel 238. The first trap position 235 is formed through an opening in the positive electrode 237a. The positive electrode 237a, as shown here, is a cylinder with an opening formed therein such that the optical cogwheel tweezers can be delivered through the opening. In one embodiment, the positive electrode 237a is 270 degrees of the cylinder with a portion of 90 degrees being removed. The positive electrode 237a then positively charges all particles passing through or over the electrode.

The positively charged particles are then drawn to one of the negative electrodes 237b and 237c. The negative electrode 237c is on by default, such that all particles are directed to the exhaust channel. When an object, such as a CTC, is captured from the biological sample in the optical cogwheel trap at the first trap position 235, the capture is detected, such as by a radiation detection device. The radiation detection device can be a photodetector. The detection causes the negative electrode 237c to be turned on. When the negative electrode 237c is on, the negative electrode 237b can be turned off or be left on, with the negative electrode 237b having a stronger negative charge than the negative electrode 237c. As such, the negative electrode 237b will attract the positively charged particle down the sample channel 238 when the particle is trapped at the first trap position 235. But otherwise, the particles will be attracted through the intermediate channel 244 to the negative electrode 237c.

Particles attracted down the sample channel 238 are then delivered to a second trap position 234. The second trap position 234 can be substantially the same as the second trap position 214 described with reference to FIG. 2A. In this embodiment, the second trap position 234 holds the particle and either allows or assist in radiation being produced, such as from a fluorophore. The positive electrode 240a and the negative electrodes 240b and 240c perform substantially the same function as the positive electrode 237a and the negative electrodes 237b and 237c. If a fluorophore is detected, the particle is directed down the sample channel 238 by negative electrode 240b. If a fluorophore is not detected, the particle is directed down the intermediate channel 242 by negative electrode 240c. Both the intermediate channel 244 and the intermediate channel 242 lead into the exhaust channel 239. The exhaust channel 239 leads back to the sample basin for reanalysis of the discarded portion of the biological sample. As above, an exhaust tank (shown with reference to FIG. 2A) can be positioned between the exhaust channel and the sample basin, such that the original biological sample can be completely analyzed prior to reintroducing the discarded portion of the biological sample.

Though the components herein are generally described with relation to a cylinder, the components may be squares, rectangles, polygons or other shapes as desired.

Figure 2C:
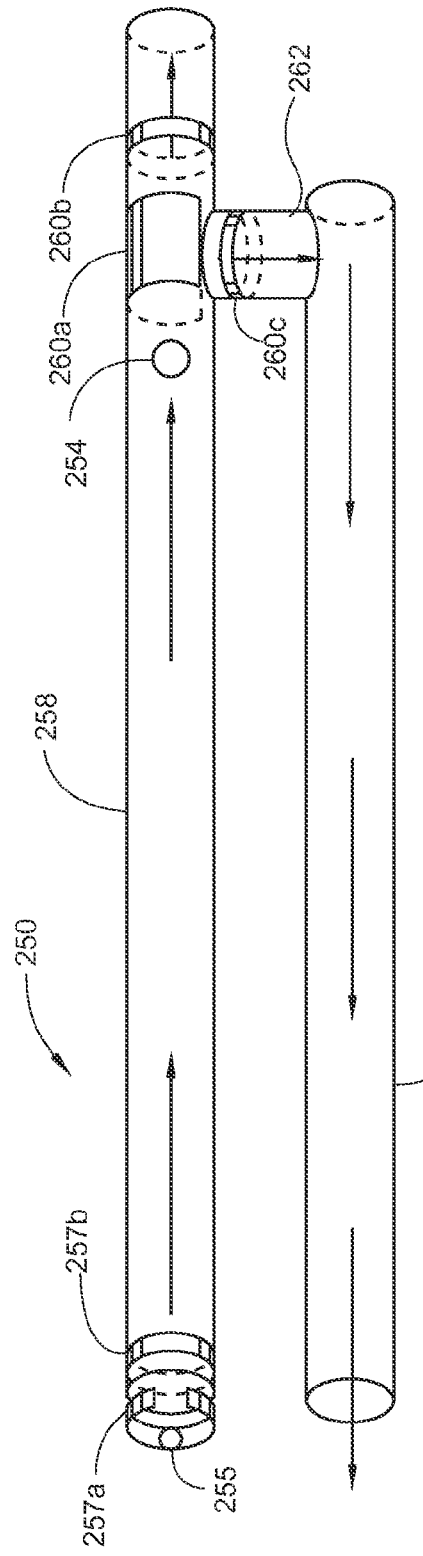

FIG. 2C describes a channel system 250 according to another embodiment. As above, the channel system 250 is an alternate embodiment which can be used in combination with or as a replacement for the channel system described with reference to FIG. 2A. The channel system 250 includes a first trap position 255, a first positive electrode 257a, first negative electrodes 257b, a sample channel 258, a second trap position 254, a second positive electrode 260a, second negative electrodes 260b and 260c, and an intermediate channel 262.

The biological sample is received in the sample basin 204, described with reference to FIG. 2A. The biological sample flows into the first trap position 255. The first trap position 255 receives optical cogwheel tweezers as described above.

The positive electrode 257a is formed or positioned at the opening of the sample channel 258. The first trap position 255 is formed through an opening in the positive electrode 257a. The positive electrode 257a can be substantially similar to the first positive electrode 237a described with reference to FIG. 2B. The positive electrode 257a positively charges all particles passing through or over the electrode.

The positively charged particles are then drawn to the negative electrode 257b. When an object, such as a CTC, is captured from the biological sample in the optical cogwheel trap at the first trap position 255, the capture is detected, such as by a radiation detection device. The radiation detection device can be a photodetector. The detection causes the negative electrode 257c to be turned on. When the negative electrode 257c is on, the negative electrode 257b can be turned off or be left on, with the negative electrode 257b having a stronger negative charge than the negative electrode 257c. As such, the negative electrode 257b will attract the positively charged particle down the sample channel 258 when the particle is trapped at the first trap position 255. But otherwise, the particles will be blocked by the particle held at the first trap position 255.

Particles attracted down the sample channel 258 are then delivered to a second trap position 254. The second trap position 254 can be substantially the same as the second trap position 214 described with reference to FIG. 2A. In this embodiment, the second trap position 254 holds the particle and either allows or assist in radiation being produced, such as from a fluorophore. The positive electrode 260a and the negative electrodes 260b and 260c perform substantially the same function as the positive electrode 240a and the negative electrodes 240b and 240c, described with reference to FIG. 2B. If a fluorophore is detected, the particle is directed down the sample channel 258 by negative electrode 260b. If a fluorophore is not detected, the particle is directed down the intermediate channel 262 by negative electrode 260c. The intermediate channel 262 leads into the exhaust channel 259. The exhaust channel 259 leads back to the sample basin for reanalysis of the discarded portion of the biological sample. As above, an exhaust tank (shown with reference to FIG. 2A) can be positioned between the exhaust channel 259 and the sample basin, such that the original biological sample can be completely analyzed prior to reintroducing the discarded portion of the biological sample.

Figure 2D:
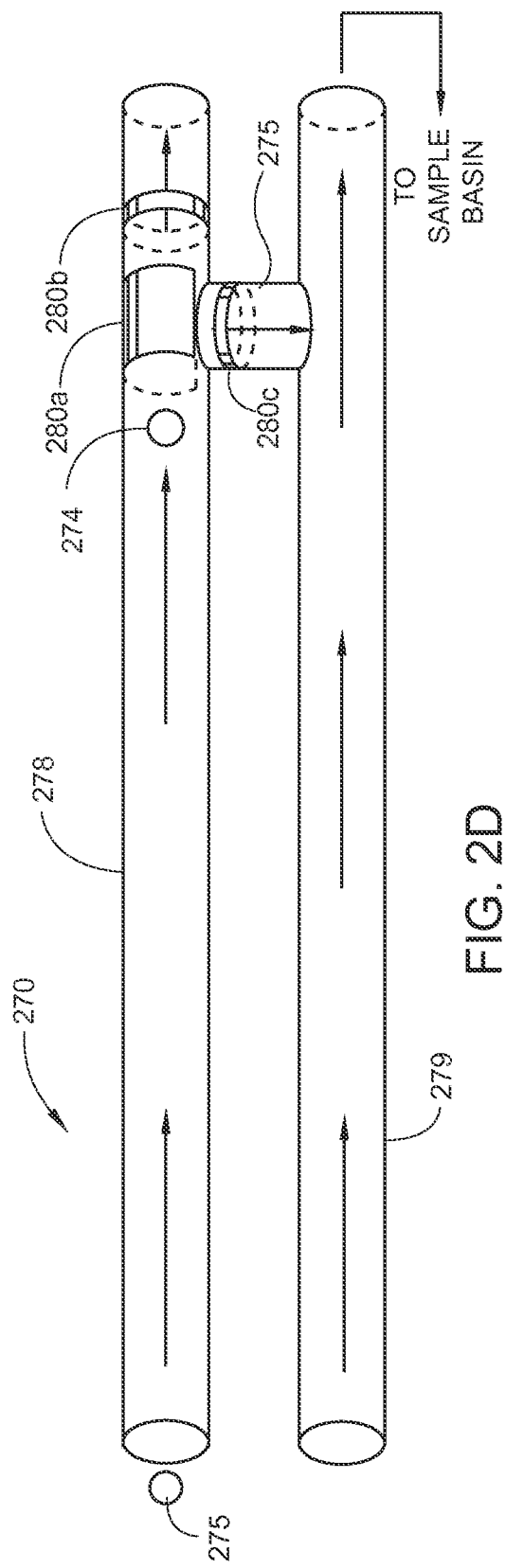

FIG. 2D describes a channel system 270 according to another embodiment. As above, the channel system 270 is an alternate embodiment which can be used in combination with or as a replacement for the channel system described with reference to FIG. 2A. The channel system 270 includes a first trap position 275, a sample channel 278, a second trap position 274, a positive electrode 280a, negative electrodes 280b and 280c, and an intermediate channel 282.

The biological sample is received in the sample basin 204, described with reference to FIG. 2A. The biological sample flows into the first trap position 275. The first trap position 275 receives optical cogwheel tweezers as described above. The first trap position 275 is formed at the opening of the sample channel 278. While a particle is held at the first trap position 275, other particles will be blocked. Once a particle is detected at the first trap position 275, it is released such that capillary action carries the particle into the sample channel 278.

Particles attracted down the sample channel 278 are then delivered to a second trap position 274. The second trap position 274 can be substantially the same as the second trap position 214 described with reference to FIG. 2A. In this embodiment, the second trap position 274 holds the particle and either allows or assist in radiation being produced, such as from a fluorophore. The positive electrode 280a and the negative electrodes 280b and 280c perform substantially the same function as the positive electrode 240a and the negative electrodes 240b and 240c, described with reference to FIG. 2B. If a fluorophore is detected, the particle is directed down the sample channel 278 by negative electrode 280b. If a fluorophore is not detected, the particle is directed down the intermediate channel 282 by negative electrode 280c. The intermediate channel 282 leads into the exhaust channel 279. The exhaust channel 279 leads back to the sample basin for reanalysis of the discarded portion of the biological sample. As above, an exhaust tank (shown with reference to FIG. 2A) can be positioned between the exhaust channel 279 and the sample basin, such that the original biological sample can be completely analyzed prior to reintroducing the discarded portion of the biological sample.

In this embodiment, the first trap position 275 and the second trap position 274 work in unison. When the first trap position 275 is not occupied, the second trap position 274 remains occupied. Thus, there is a fluid back pressure that prevents particles from entering the sample channel until the first trap position 275 position is occupied again. When the first trap position 275 is occupied, a signal is sent to the second trap position 274, such that the positive electrode 280a and the negative electrodes 280b and 280c direct the particle trapped at the second trap position 274 according to the detection of a fluorophore.

Figure 3:
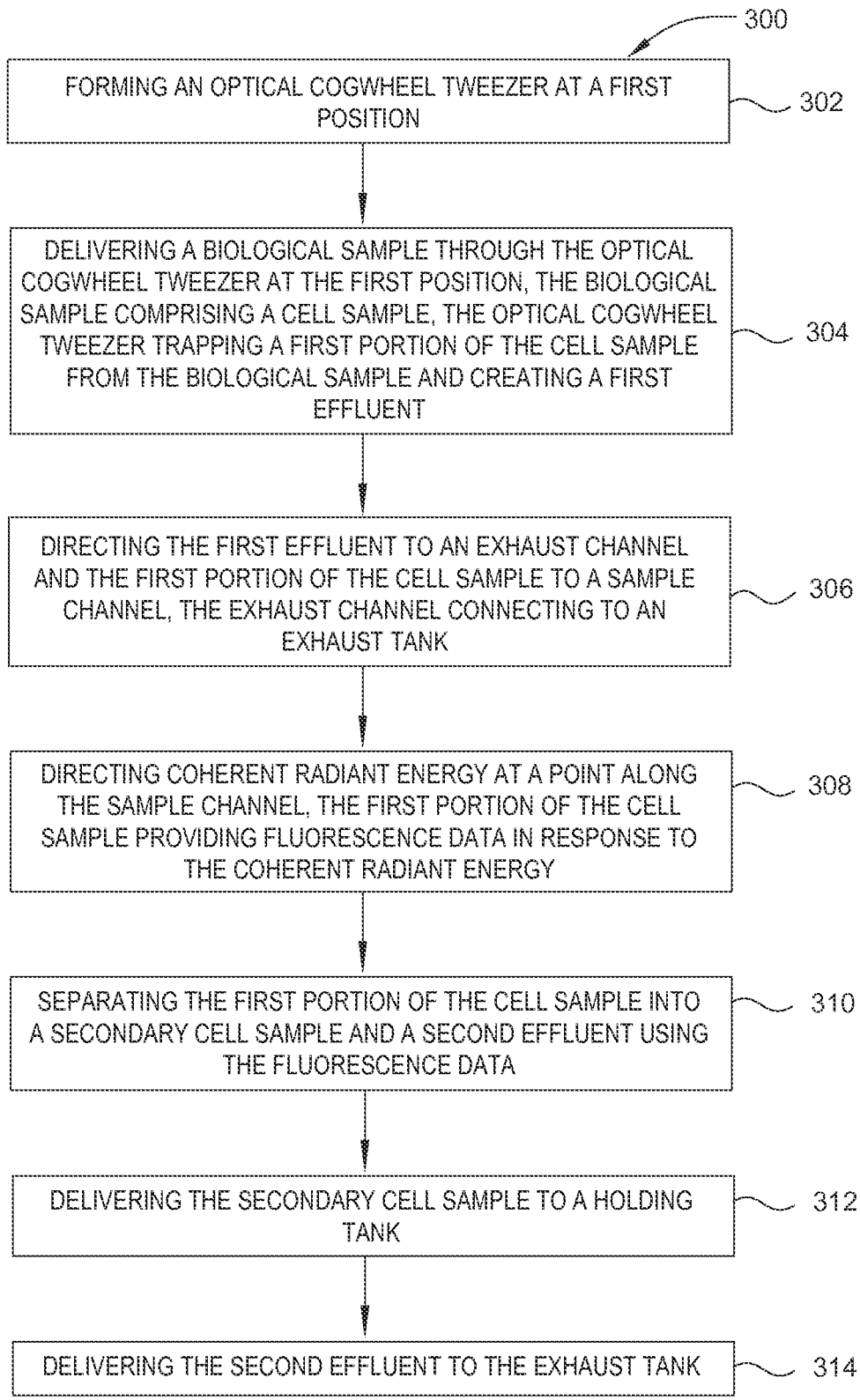
FIG. 3 is a flow diagram of a cell sorting method, according to one embodiment.

FIG. 3 is a flow diagram of a cell sorting method 300, according to one embodiment. The method 300 includes forming one or more optical cogwheel tweezers at a first position, at 302; delivering a biological sample through the optical cogwheel tweezers at the first position, the biological sample comprising a cell sample, the optical cogwheel tweezers trapping a first portion of the cell sample from the biological sample and creating a first effluent, at 304; directing the first effluent to an exhaust channel and the first portion of the cell sample to a sample channel, the exhaust channel connecting to an exhaust tank, at 306; directing coherent radiant energy at a point along the sample channel, the first portion of the cell sample providing fluorescence data in response to the coherent radiant energy, at 308; separating the first portion of the cell sample into a secondary cell sample and a second effluent using the fluorescence data, at 310; delivering the secondary cell sample to a holding tank at 312; delivering the second effluent to the exhaust tank, at 314. The size-selective filtering can be repeated one or more times using the first effluent and the second effluent collected in exhaust tank.

The method 300 begins at 302 by forming one or more optical cogwheel tweezers at a first position. The optical cogwheel tweezers is formed as described above, with reference to FIG. 2. The optical cogwheel tweezers can be formed at any position such that the optical cogwheel tweezers interrupt the path of a biological sample. In one example, the optical cogwheel tweezers are formed at the entrance to a sample channel.

The biological sample is then delivered at 304 through the optical cogwheel tweezers at the first position. The optical cogwheel tweezers form a size selective barrier for smaller components of the biological sample, such as hemocytes and leukocytes, to pass freely. However, larger components of the biological sample, such as CTCs will be captured. The optical cogwheel tweezers thus trap a first portion of the cell sample (e.g., the CTCs) from the biological sample. The biological sample can be labeled using a fluorophore, as noted above, or by radiolabelling.

A fluorophore, as used herein, is a molecule which fluoresces in the presence of radiation. The fluorophore or radioisotope (in the case of radiolabelling) can be targeted to cells in the biological sample through the use of conjugated antibodies, conjugated ligands, targeted miscibility, protein cleavage, intracellular processing (as in the case of nucleotide triphosphate formation) or other methods of selective accumulation. The fluorophore or radioisotope labeling is targeted to a secondary trait which is unique to the CTCs, as compared to other components or cells in the biological sample (e.g., conjugated antibody targeting a cell surface marker for epithelial cells, a conjugated ligand for a receptor only expressed in actively proliferating cells, etc.). Once the cells are marked with the fluorophore or radiolabelled, the radiation production can be detected and used to differentiate the targeted cell type from non-targeted cell types.

The first effluent is then directed to an exhaust channel and the first portion of the cell sample to a sample channel at 306. The exhaust channel is fluidly connected to an exhaust tank. The first portion of the cell sample is then redirected to a sample channel. The remaining portion of the biological sample which is not redirected (i.e., a first effluent) is then redirected to an exhaust tank. Both the first portion of the cell sample and the remaining portion of the biological sample can be redirected using a flow control device, such as the dielectrophoresis device described above. In another embodiment, the first portion of the cell sample is redirected using a microactuator to create a physical barrier to further flow in one or the two directions (e.g., the direction of the sample channel or the exhaust channel).

Coherent radiant energy is directed at a point along the sample channel at 308. As the cell sample passes under the radiation from the radiation source, the cell will be held in position at the second trap position as described above. The coherent radiation thus creates a second trap that allows the cells to be analyzed without significantly affecting survivability of the sample.

Optionally, the first portion of the cell sample is then separated into a secondary cell sample and a second effluent using the fluorescence data at 310. In the case of a fluorophore, the first portion of the cell sample will provide fluorescence data in response to the coherent radiant energy. In the case of radiolabelling, the radioisotope will provide radiation as indicated by the type of radioisotope. The fluorescence or other radiation can then be used to differentiate between cells held in the radiation that are labeled and unlabelled cells held in the radiation.

The secondary cell sample can then be delivered to a holding tank, at 312. The secondary cell sample contains a viable cell sample, selected based on both size and a secondary trait which is unique to the desired cells. In the case of CTCs in a blood sample, this can include active growth, presence of mRNA, cell surface markers not native to hemocytes or leukocytes, or others. The secondary cell sample is thus delivered to a holding tank for further analysis.

The second effluent is then delivered to the exhaust tank, at 314. The second effluent can flow through the intermediate channels to the exhaust channel, described with reference to FIG. 2. This sample is separated using the flow control device described above to further purify the portion of the biological sample in the sample channel. Unlabelled cells are then categorized as the second effluent and delivered to the exhaust tank.

The size-selective filtering can be repeated one or more times using the first effluent and the second effluent collected in the exhaust tank. To prevent inadvertent loss of the desired cells, such as CTCs, the biological sample that has collected in the exhaust tank can be reprocessed. In this way, the biological sample is processed quickly in an efficient, selective and precise manner to determine overall quantity of the desired cells.

Using the method described above, larger and morphologically different cells in a biological sample can be separate based on an initial size filter followed by finer separation based on known characteristics. By separating grossly based on size followed by fine separation, the quantity of CTCs in a small or low concentration sample. Further, the quantity of CTCs can be determined in a fast and efficient manner, for early diagnosis in real time. Finally, the above method concentrates the CTCs in the sample and preserves viability of the cells for further testing.

Embodiments described herein relate to devices, systems and methods using optical cogwheel tweezers for separating CTCs from blood cells using optical trapping, such as optical cogwheel tweezers. The devices, systems and methods described herein use a pre-filtration of the biological sample through optical cogwheel tweezers and separating by size, prior to finer detection techniques. As such, the samples can be process more quickly while maintaining the precision necessary for detection of CTCs, even in small samples. Further, the cells derived from the above devices, systems and methods remain viable for various growth analysis.

While the foregoing is directed to embodiments of the present devices, systems and methods, other and further embodiments of the devices, systems and methods may be devised without departing from the basic scope thereof, and the scope thereof is determined by the claims that follow.

What is claimed is:

1. A method of cell sorting, comprising:
   forming one or more optical cogwheel tweezers at a first position of a sample basin, the optical cogwheel tweezers having an aperture;
   size-selectively filtering a biological sample, the filtering comprising:
      delivering a biological sample through the optical cogwheel tweezers at the first position, the biological sample comprising a cell sample, the optical cogwheel tweezers trapping a first portion of the cell sample from the biological sample and creating a first effluent, the first effluent being the remainder of the biological sample after removing the first portion of the cell sample;
      directing the first effluent from the first position through an exhaust channel to an exhaust tank and the first portion of the cell sample through a sample channel using a flow control device in communication with the sample basin, a flow direction of the first effluent being parallel to a flow direction of the first portion of the cell sample;
      directing coherent radiant energy at a point along the sample channel between the sample basin and a holding tank, the first portion of the cell sample providing fluorescence data in response to the coherent radiant energy;
      separating the first portion of the cell sample into a secondary cell sample and a second effluent using the fluorescence data;
      delivering the secondary cell sample to a holding tank; and
      delivering the second effluent from the sample channel through an intermediate channel and the exhaust channel to the exhaust tank; and
   repeating the size-selective filtering one or more times using the first effluent and the second effluent collected in exhaust tank.

2. The method of claim 1, further comprising detecting circulating tumor cells (CTCs), hemocytes and lymphocytes.

3. The method of claim 2, wherein the size selective filtering is repeated until the biological sample is clear of CTCs.

4. The method of claim 1, wherein the cell sample in the biological sample is tagged with a fluorophore.

5. The method of claim 4, wherein the fluorophore is conjugated to be selective for actively dividing cells.

6. The method of claim 1, wherein the aperture created by the optical cogwheel tweezers is between about 10 um and about 30 um wide.

7. The method of claim 1, wherein the biological sample is delivered at approximate in vivo rates.

8. The method of claim 1, wherein directing the first effluent to the exhaust channel and the first portion of the cell sample to the sample channel comprises:
   detecting the first portion of the cell sample at the first trap position; and
   forming a first electric field and a second electric field in response to detecting the first portion, the first electric field positioned proximate an entrance to the exhaust channel and the second electric field positioned proximate an entrance to the sample channel, the second electric field being stronger than the first electric field.

9. The method of claim 8, wherein the first electric field is stronger than the second electric field in the presence of the first effluent.

* * * * *